United States Patent
Lv et al.

(10) Patent No.: US 11,723,630 B2
(45) Date of Patent: Aug. 15, 2023

(54) METHOD FOR POSITIONING KEY FEATURES OF A LENS BASED ON OCULAR B-MODE ULTRASOUND IMAGES

(71) Applicant: Sichuan University, Chengdu (CN)

(72) Inventors: Jiancheng Lv, Chengdu (CN); Yong Wang, Chengdu (CN); Yongsheng Sang, Chengdu (CN); Dezhong Peng, Chengdu (CN); Xi Peng, Chengdu (CN); Yanan Sun, Chengdu (CN); Zhenan He, Chengdu (CN); Qing Ye, Chengdu (CN); Mao Li, Chengdu (CN); Quanhui Liu, Chengdu (CN)

(73) Assignee: Sichuan University, Chengdu (CN)

( * ) Notice: Subject to any disclaimer, the term of this patent is extended or adjusted under 35 U.S.C. 154(b) by 196 days.

(21) Appl. No.: 17/301,615

(22) Filed: Apr. 9, 2021

(65) Prior Publication Data
US 2021/0353262 A1    Nov. 18, 2021

(30) Foreign Application Priority Data

May 14, 2020  (CN) .......................... 202010408004.9

(51) Int. Cl.
| | |
|---|---|
| *A61B 8/08* | (2006.01) |
| *G16H 30/20* | (2018.01) |
| *G16H 30/40* | (2018.01) |
| *A61B 8/10* | (2006.01) |
| *G06N 3/084* | (2023.01) |

(52) U.S. Cl.
CPC .............. *A61B 8/5246* (2013.01); *A61B 8/10* (2013.01); *A61B 8/5223* (2013.01); *G06N 3/084* (2013.01); *G16H 30/20* (2018.01); *G16H 30/40* (2018.01)

(58) Field of Classification Search
None
See application file for complete search history.

(56) References Cited

U.S. PATENT DOCUMENTS

| | | | |
|---|---|---|---|
| 2020/0194108 A1* | 6/2020 | Podilchuk | G06V 10/82 |
| 2021/0059756 A1* | 3/2021 | Kim | G16H 50/30 |
| 2022/0156941 A1* | 5/2022 | He | A61B 3/12 |

* cited by examiner

Primary Examiner — Jonathan Cwern
(74) Attorney, Agent, or Firm — Bayramoglu Law Offices LLC

(57) ABSTRACT

A method for positioning key features of a lens based on ocular B-mode ultrasound images includes: acquiring and preprocessing the ocular B-mode ultrasound images to obtain a preprocessed B-mode ultrasound image, eyeball coordinates and lens coordinates; sending the preprocessed B-mode ultrasound image, the eyeball coordinates and the lens coordinates into a trained target detection network YOLOv3 to obtain eyeball position images and lens position images; substituting the eyeball position images and the lens position images into a trained feature extraction network group to obtain image features and feature coordinates corresponding to the eyeball position images and the lens position images, respectively; substituting the image features into a trained collaborative learning network to screen key image features; and marking a feature coordinate corresponding to the key image features on the ocular B-mode ultrasound images to complete positioning the key features of the lens.

10 Claims, 4 Drawing Sheets

METHOD FOR POSITIONING KEY FEATURES OF A LENS BASED ON OCULAR B-MODE ULTRASOUND IMAGES

CROSS REFERENCE TO THE RELATED APPLICATIONS

This application is based upon and claims priority to Chinese Patent Application No. 202010408004.9, filed on May 14, 2020, the entire contents of which are incorporated herein by reference.

TECHNICAL FIELD

The present invention relates to the technical field of medical image recognition, and more particularly, to a method for positioning key features of a lens based on ocular B-mode ultrasound images.

BACKGROUND

The lens is an important refractive structure in the eyeball as well as an only refractive media with the adjustment ability, of which the main function is to enable an eye to focus on objects at various distances. By changing the diopter, light from nearby or distant objects can be accurately focused on a retina. Regular inspection of the state of the lens helps prevent the lens from abnormalities, thereby avoiding permanent damage to an optic nerve.

Generally, ocular B-mode ultrasound images are used to identify the state of the lens. Based on the lens part in the ocular B-mode ultrasound images, doctors determine whether patients' lens is in a healthy state depending on experience. Due to the complexity of the ocular B-mode ultrasound images, however, such determination is just a general one about an overall state, failing to enable the doctor to understand a specific state and a feature condition of the lens. Thus, it is difficult for the doctors to make the best medical plan in time for treating ocular disorders. Regarding this, some medical researchers have tried to distinguish and position the features of the lens, so as to study specific occurring signs and changing laws of lens opacity.

Human ocular tissue is complicated. Additionally, ocular changes vary from patient to patient, for example, some patients have a color change in a certain part of the lens, some patients have a color change in two parts of the lens, and some patients have no obvious color change in the lens. This makes it difficult for medical researchers to accurately position the corresponding features from each ocular B-mode ultrasound image, and also difficult to accurately extract the corresponding features from the human ocular tissue, which produces interference factors during the process of the medical researchers finding the cause of a disease, thereby affecting smooth progress of research and trials.

SUMMARY

In view of the above-mentioned shortcomings in the prior art, the present invention provides a method for positioning key features of a lens based on ocular B-mode ultrasound images, which can solve the problem in the prior art that it is difficult to position and determine the feature of the lens.

To solve the above technical problem, the present invention adopts the following technical solution:

A method for positioning key features of a lens based on ocular B-mode ultrasound images is provided, including the following steps:

S1: acquiring and preprocessing the ocular B-mode ultrasound images to obtain preprocessed B-mode ultrasound image, eyeball coordinates and lens coordinates;

S2: fusing and then sending the preprocessed B-mode ultrasound images and the eyeball coordinates into a trained target detection network YOLOv3 to obtain eyeball position images; sending the preprocessed B-mode ultrasound images and the lens coordinates into another trained target detection Network YOLOv3 to obtain lens position images;

S3: substituting the eyeball position images and the lens position images into a trained feature extraction network group to obtain image features and feature coordinates corresponding to the eyeball position images and the lens position images, respectively;

S4: substituting the image features into a trained collaborative learning network to screen key image features; and S5: marking a feature coordinate corresponding to the key image features on the ocular B-mode ultrasound images to complete positioning the key features of the lens.

The method for positioning the key features of the lens based on ocular B-mode ultrasound images provided in the present invention has the following advantages.

In the present invention, the target detection network is set to process the original ocular B-mode ultrasound images, which solves the problems that the eyeball part only occupies a small part of the original images and there exists strong echo interference in irrelevant background, so as to extract the position images corresponding to the eyeball and the lens. Through the overall evaluation of the eyeball region and the monitoring of the lens region, different feature regions may be extracted, which increases the difficulty of determination. With regard to this, the different feature extraction networks are adopted to separately extract the features corresponding to the eyeball region and the lens region and combine with the collaborative learning network to effectively ensure the accuracy of positioning the feature region.

The method for positioning key features of a lens provided herein identifies different features of the lens by using the deep learning technology, such that abnormal features of the lens can be quickly and accurately positioned, which is convenient for further evaluation of the state of the lens, thereby contributing to related research and teaching references.

DETAILED DESCRIPTION OF THE EMBODIMENTS

The present invention will be further explained below in conjunction with the drawings.

Figure 1:
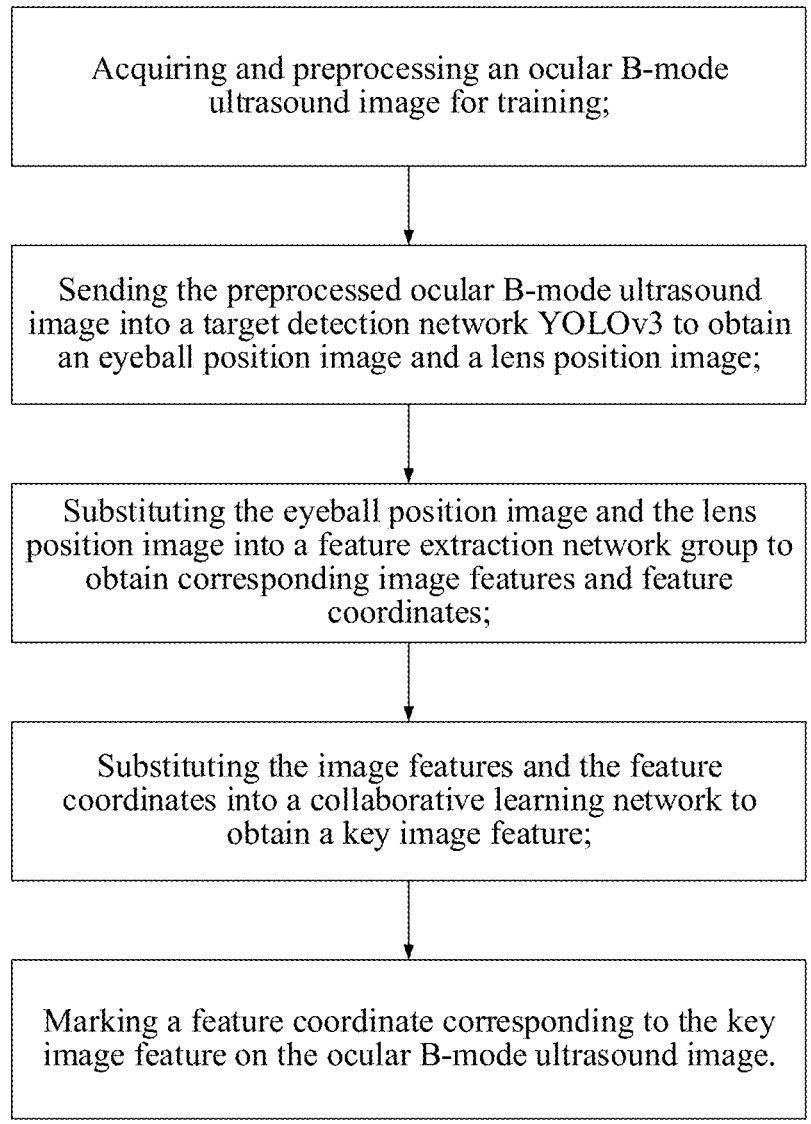
FIG. 1 is a flow chart of a method of the present invention.

FIG. 1 is a flowchart of a method for positioning key features of a lens based on ocular B-mode ultrasound images.

Figure 2:
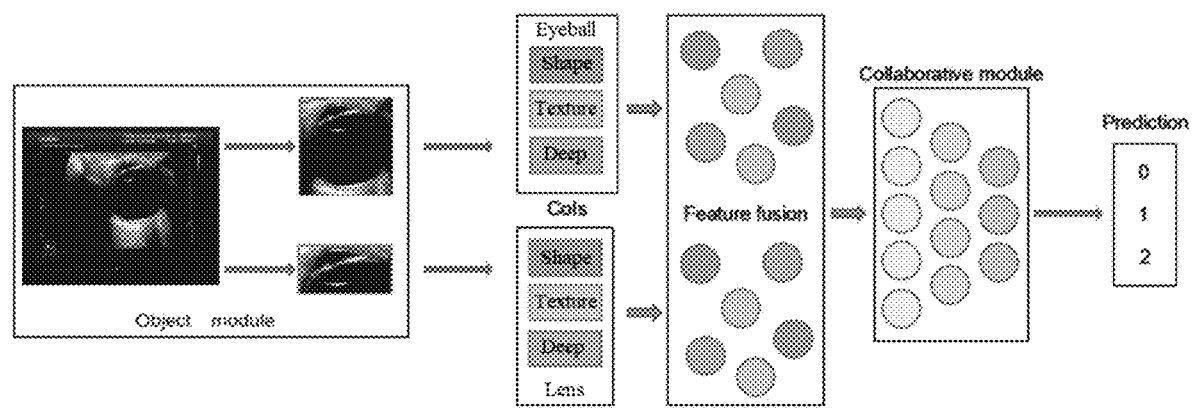
FIG. 2 is a principle diagram of the present invention.
Figure 3:
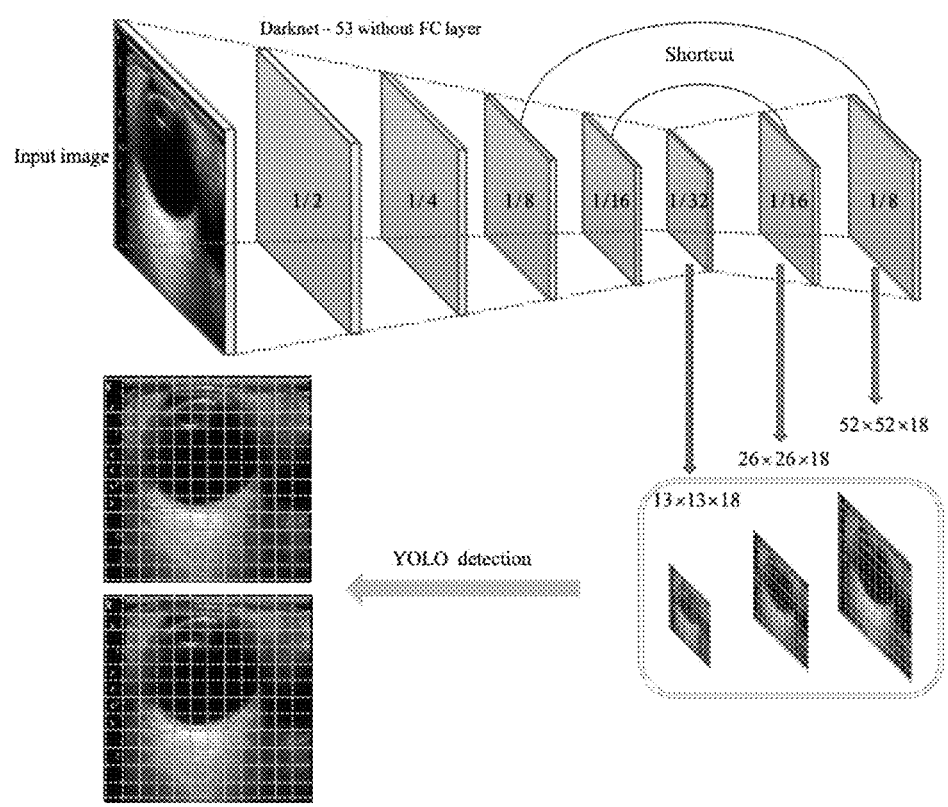
FIG. 3 is a schematic diagram of a detection principle of a target detection network YOLOv3.

The method for positioning the key features of the lens based on the ocular B-mode ultrasound images provided in the present invention will be described below in conjunction with the embodiments, as shown in FIGS. 2 and 3, including the following steps.

S1: the ocular B-mode ultrasound images are acquired and preprocessed to obtain preprocessed B-mode ultrasound images, eyeball coordinates and lens coordinates.

Further, a method of preprocessing the ocular B-mode ultrasound images includes:

S1-1: all acquired ocular B-mode ultrasound images are converted into image files of a set size and a set format to obtain an image file set.

Generally, original ocular B-mode ultrasound images, typically Digital Imaging and Communications in Medicine (DICOM) images, are converted to a portable network graphic (PNG) format with a resolution of 720×576 for easy processing.

S1-2: the image file set is divided into a target detection group for training a target detection network YOLOv3 and a feature extraction group for training a feature extraction network.

S1-3: the eyeball coordinates and the lens coordinates in an image file set of the target detection group are marked to enable the target detection network YOLOv3 to generate eyeball position images corresponding to the eyeball coordinates and lens position images corresponding to the lens coordinates.

Generally, coordinates of an upper left corner and a lower right corner of an eyeball and coordinates of an upper left corner and a lower right corner of a lens are adopted to mark the eyeball position and the lens position, respectively.

S2: the preprocessed B-mode ultrasound image and the eyeball coordinates are fused and then sent into a trained target detection network YOLOv3 to obtain the eyeball position images; and the preprocessed B-mode ultrasound image and the lens coordinates are sent into another trained target detection Network YOLOv3 to obtain the lens position images.

Further, Step S2 includes the following steps.

S2-1: the eyeball coordinates are normalized, and the preprocessed B-mode ultrasound image is adjusted to a target size.

Specifically, in an embodiment, the target size of the B-mode ultrasound image is 416×416.

S2-2: the B-mode ultrasound image adjusted to the target size is sent into a backbone network DarkNet53 to obtain a feature dataset including a plurality of modules.

In an embodiment, the feature dataset includes five modules, compositions of which are as follows:

a first module: including two 3×3 convolution layers, and one residual block;

a second module: including one 3×3 convolution layer, and two residual blocks;

a third module: including one 3×3 convolution layer, and eight residual blocks;

a fourth module: including one 3×3 convolution layer, and eight residual blocks;

a fifth module: including one 3×3 convolution layer, and four residual blocks;

where, each residual block includes one 1×1 convolution layer and one 3×3 convolution layer; and a shortcut connection is provided between an input and an output.

S2-3: the plurality of modules in the feature dataset are spliced with each other to obtain corresponding splicing results.

S2-4: convolution processing is performed on the splicing results to obtain possible eyeball positions.

In an embodiment, specifically, a method of splicing and processing includes:

S2-4.1: an output size of the fifth module is adjusted to 13×13, and an output result of the fifth module is enabled to successively pass through one convolution block, one 3×3 convolution layer and one 1×1 convolution layer to obtain a first eyeball position prediction, where the one convolution block includes one 1×1 convolution layer, one 3×3 convolution layer, one 1×1 convolution layer, one 3×3 convolution layer, and one 1×1 convolution layer.

S2-4.2: an output size of the fourth module is adjusted to 26×26, and a first splicing operation is performed on an output result of the fifth module after passing through one convolution block, one 1×1 convolution layer and one upsampling layer and an output result of the fourth module.

S2-4.3: an output result of the first splicing operation is enabled to pass through one convolution block, one 3×3 convolution layer and one 1×1 convolution layer to obtain a second eyeball position prediction.

S2-4.4: an output size of the third module is adjusted to 26×26, and a second splicing operation is performed on the output result of the first splicing operation after passing through one convolution block, one 1×1 convolution layer and one upsampling layer and an output result of the third module.

S2-4.5: an output result of the second splicing operation is enabled to pass through one convolution block, one 3×3 convolution layer and one 1×1 convolution layer to obtain a third eyeball position prediction.

S2-5: all the possible eyeball positions are substituted into the target detection network YOLOv3 to enable the target detection network YOLOv3 to use feature maps of the three eyeball position predictions to obtain the eyeball position images.

Specifically, the three eyeball position predictions are substituted into the target detection network YOLOv3, so that the target detection network YOLOv3 uses the feature maps of the three eyeball position predictions to perform predictions, and generates the corresponding eyeball feature images, and the output sizes thereof are 13×13×6, 26×26×6 and 52×52×6, respectively, the number 6=(4+1+1), which represents a bounding box position coordinates, a bounding box confidence and a class probability, respectively.

In actual operation, the bounding box position is expressed by a coordinate of the center point of the bounding box and a width and a height of the bounding box. The confidence score is used to reflect whether to contain an object and the accuracy of the bounding box position in case of containing an object.

A loss function of the target detection network YOLOv3 is a weighted sum of the bounding box position, the bounding box confidence and the class probability, where the bounding box position uses the mean square error, the bounding box confidence and the class probability use the cross entropy.

S2-6: steps S2-1 to S2-5 are repeatedly performed on the lens coordinates to obtain the lens position images.

S3: the eyeball position images and the lens position images are substituted into the trained feature extraction network to obtain image features and feature coordinates corresponding to the eyeball position images and the lens position images, respectively.

Further, the step of obtaining the trained feature extraction network includes:

S3-1: the eyeball position images and the lens position images are divided into training sets, validation sets and test sets, respectively.

S3-2: the training sets corresponding to the eyeball position images and the lens position images are separately sent into the corresponding feature extraction network for training to separately obtain the trained feature extraction network.

Figure 4:
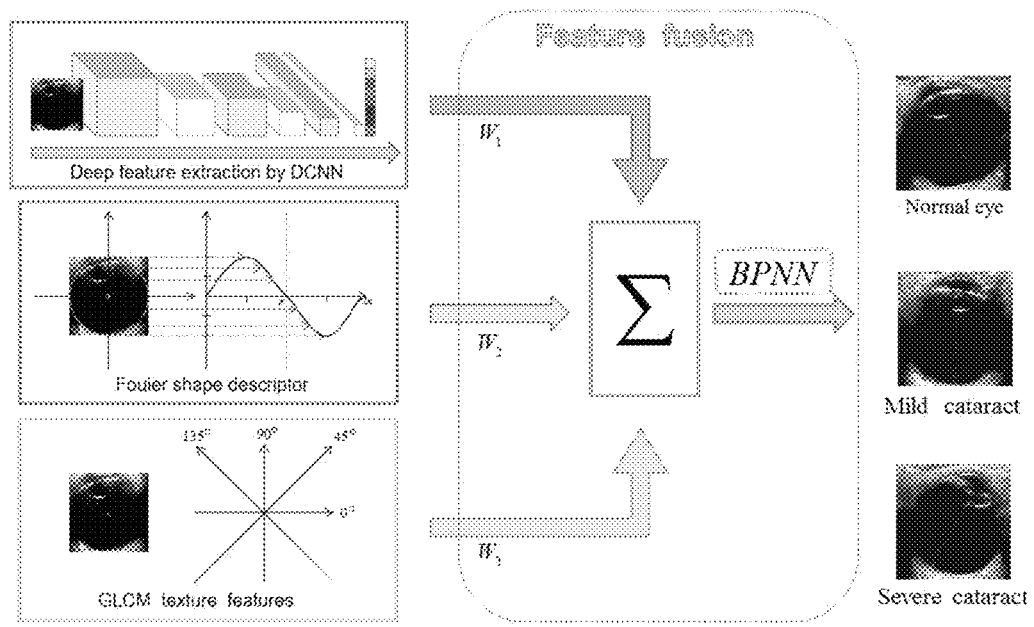
FIG. 4 is a schematic diagram of a logical structure of a COI+BPNN module.
Figure 6:
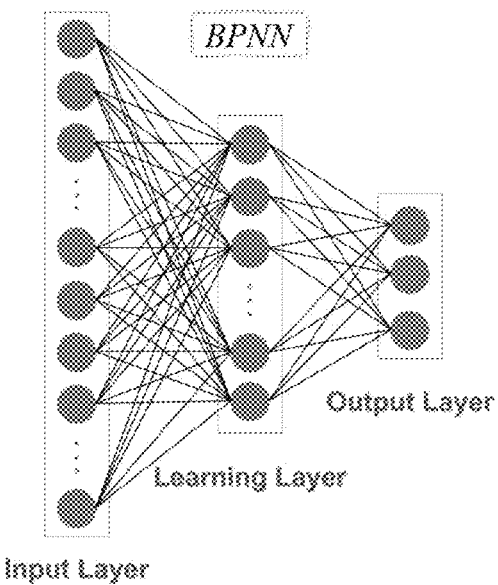
FIG. 6 is a schematic diagram of a logical structure of a back propagation neural network BPNN.

Specifically, the feature extraction network includes an Eyeball COI+BPNN module corresponding to the eyeball position images and a Lens COI+BPNN module corresponding to the lens position images. As shown in FIG. 4, the COI+BPNN module includes a back propagation neural network BPNN. As shown in FIG. 6, the back propagation neural network is trained by a convolutional neural network DenseNet161, a Fourier descriptor, and a gray-level co-occurrence matrix (GLCM).

Specifically, the step of training the feature extraction network includes: S3-2-1: the eyeball position images and the lens position images are adjusted to a required size and are then subjected to a deformation processing to obtain position images after the deformation processing.

The required size is 128×128. The deformation processing includes random horizontal flip, random rotation of 0-10 degrees, brightness adjustment, color jitter, and normalization.

S3-2-2: the position images after the deformation processing are substituted into the Fourier descriptor to obtain 36-dimensional shape features corresponding to the position images.

The operation process of the Fourier descriptor includes:

A1: a gravity center of a binary image is determined;

A2: the distance between the gravity center and a point which moves along a boundary, and a geodesic distance of the point are drawn; and A3: Fourier transform is performed on the image.

S3-2-3: the position images after the deformation processing are substituted into the gray-level co-occurrence matrix, and energies, contrasts, entropies, and inverse differences of the gray-level co-occurrence matrix GLCM in four directions are calculated to obtain 16-dimensional texture features corresponding to the position images.

Generally, a multi-channel image is first converted into a gray-level image to facilitate the identification of the heterogeneity of the lens and the surrounding strong echo.

Generally, four directions (0, 45, 90 and 135) are used to obtain the 16-dimensional GLCM texture descriptor of each image. Since the texture features generally have rotation invariance and strong resistance to noise, calculating the features in four directions can fully guarantee effective description of surface properties of an object corresponding to the image or the image region.

Figure 5:
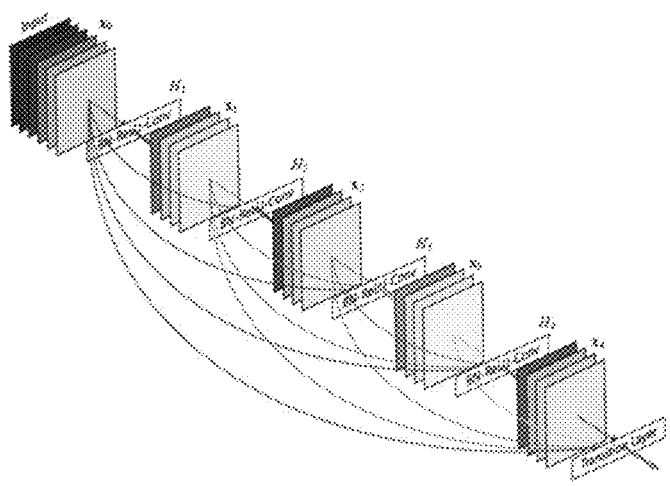
FIG. 5 is a schematic diagram of a logical structure of a convolutional neural network DenseNet161.

S3-2-4: an imageNet dataset is adopted to pre-train the convolutional neural network DenseNet161, as shown in FIG. 5, the position images after the deformation processing are substituted into the trained convolutional neural network DenseNet161, and 2208-dimensional features of a penultimate layer of the convolutional neural network DenseNet161 corresponding to the position images are obtained and used as the depth features.

S3-2-5: the shape features, the texture features and the depth features are fused and then substituted into the back propagation neural network BPNN for training to obtain the trained back propagation neural network BPNN and the trained feature extraction network.

In an embodiment, a convergence error is set to 0.0004 and a learning rate is set to 0.001 for training. The training is stopped when the error on the validation set is less than 0.0004, so as to achieve a balance between time cost and performance.

S3-3: the validation sets corresponding to the eyeball position images and the lens position images are separately sent into the corresponding trained feature extraction network to obtain corresponding lens features.

S3-4: states of the lens are evaluated according to the lens features, evaluation results are compared with real labels in the validation sets, and a validation accuracy rate is recorded.

A prediction result is compared with the real labels in the validation sets, that is, comparing a similarity of image features is performed so as to obtain the validation accuracy rate.

S3-5: steps S3-2 to S3-4 are repeatedly performed according to a set number of times, weights of two feature extraction networks with a highest validation accuracy rate during a repeated performing process are saved, and the two feature extraction networks are taken as the target feature extraction network group, and the weights are substituted into the test sets to obtain a test accuracy rate of the target feature extraction network group.

In an embodiment, the set number of times is 200 epochs, which ensures a sufficient selection amount, thereby ensuring the prediction accuracy rate.

S3-6: the test accuracy rate is compared with a target value, and when the test accuracy rate is less than the target value, step S3-5 is repeatedly performed until the validation accuracy rate of the target feature extraction network group is greater than or equal to a target value, and the target feature extraction network group corresponding to the test accuracy rate is used as the trained feature extraction network group.

In an embodiment, the target value of the test accuracy rate is 90%. Being greater than 90% means that the prediction result has a relatively high confidence level and the turbidity classification is relatively accurate. Accordingly, the trained feature extraction network group can be adopted. The actual result is 95%, meaning that the result has a relatively high confidence level and the classification result is relatively accurate.

The features of the lens position images and the eyeball position images are separately extracted by using the feature extraction network group, such that the lens features are extracted at both global and local levels, which ensures the accuracy of positioning.

S4: the image features are substituted into a trained collaborative learning network to screen a key image feature.

Figure 7:
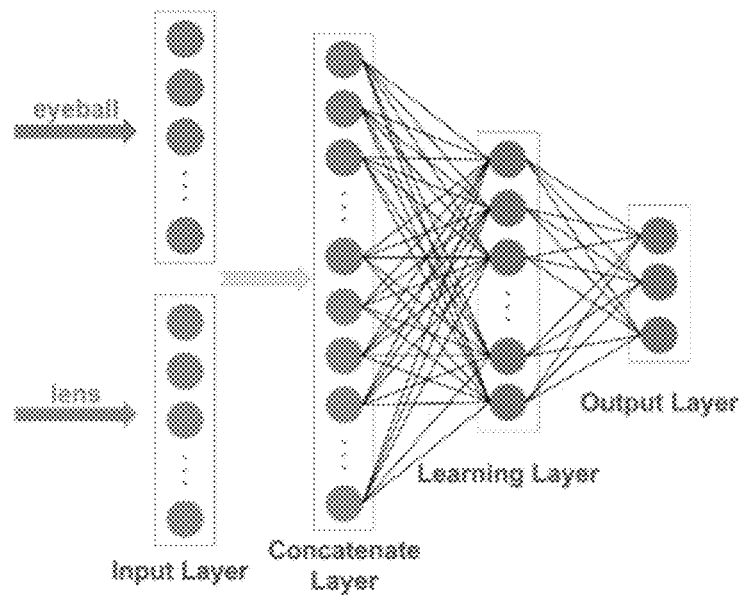
FIG. 7 is a schematic diagram of a logical structure of a collaborative learning network.

Specifically, as shown in FIG. 7, the step of obtaining the trained collaborative learning network includes:

S4-1: a learning layer of the back propagation neural network BPNN in the COI+BPNN module is used as an input layer of the collaborative learning network.

S4-2: two fully connected layers are added behind the input layer of the collaborative learning network to be used as a learning layer and an output layer, where a result obtained from the output layer is the prediction result.

S4-3: the features correspondingly obtained by the Eyeball COI+BPNN module and the Lens COI+BPNN module are linked and then substituted into the input layer of the collaborative learning network to obtain the trained collaborative learning network.

S5: a feature coordinate corresponding to the key image features is marked on the ocular B-mode ultrasound images to complete positioning the key features of the lens.

The method for positioning the key features of the lens provided herein identifies different features of the lens by using the deep learning technology, such that abnormal features of the lens can be quickly and accurately positioned, which is convenient for further evaluation of the state of the lens, thereby contributing to related research and teaching references.

The specific embodiments of the present invention are described above to facilitate those skilled in the art to understand the present invention. However, it should be noted that the present invention is not limited to the scope of the specific embodiments. For those skilled in the art, as long as various changes are within the spirit and scope of the present invention defined and determined by the appended claims, these changes are obvious, and all solutions that are made taking inventive concepts of the present invention shall fall within the scope of protection of the present invention.

What is claimed is:

1. A method for positioning key features of a lens based on ocular B-mode ultrasound images, comprising:
    S1: acquiring and preprocessing the ocular B-mode ultrasound images to obtain a preprocessed B-mode ultrasound image, eyeball coordinates and lens coordinates;
    S2: fusing the preprocessed B-mode ultrasound image and the eyeball coordinates and then sending the preprocessed B-mode ultrasound image and the eyeball coordinates into a trained target detection network to obtain eyeball position images; sending the preprocessed B-mode ultrasound image and the lens coordinates into the trained target detection network to obtain lens position images;
    S3: substituting the eyeball position images and the lens position images into a trained feature extraction network group to obtain image features and feature coordinates corresponding to the eyeball position images and the lens position images, respectively;
    S4: substituting the image features into a trained collaborative learning network to screen key image features; and
    S5: marking a feature coordinate corresponding to the key image feature on the ocular B-mode ultrasound images to complete positioning the key features of the lens.

2. The method according to claim 1, wherein a method of preprocessing the ocular B-mode ultrasound images comprises:
    S1-1: converting the ocular B-mode ultrasound images into image files of a set size and a set format to obtain an image file set;
    S1-2: dividing the image file set into an image file subset of a target detection group for training a target detection network and an image file subset of a feature extraction group for training a feature extraction network; and
    S1-3: marking the eyeball coordinates and the lens coordinates in the image file subset of the target detection group.

3. The method according to claim 2, wherein the eyeball coordinates comprise coordinates of an upper left corner and a lower right corner of an eyeball; the lens coordinates comprise coordinates of an upper left corner and a lower right corner of the lens.

4. The method according to claim 3, wherein a specific step of training the target detection network comprises:
    S2-1: normalizing the eyeball coordinates, and adjusting the preprocessed B-mode ultrasound image to a target size to obtain an adjusted B-mode ultrasound image;
    S2-2: sending the adjusted B-mode ultrasound image into a backbone network to obtain a feature dataset comprising a plurality of modules;
    S2-3: splicing the plurality of modules in the feature dataset with each other to obtain splicing results corresponding to the plurality of modules;
    S2-4: performing a convolution processing on the splicing results to obtain possible eyeball positions;
    S2-5: substituting the possible eyeball positions into the target detection network to enable the target detection network to use feature maps of three eyeball position predictions to obtain the eyeball position images; and
    S2-6: repeatedly performing steps S2-1 to S2-5 on the lens coordinates to obtain the lens position images.

5. The method according to claim 1, wherein a specific step of obtaining the trained feature extraction network group comprises:
    S3-1: dividing the eyeball position images and the lens position images into training sets, validation sets and test sets, respectively;
    S3-2: separately sending the training sets corresponding to the eyeball position images and the lens position images into the feature extraction network separately corresponding to the eyeball position images and the lens position images for training to separately obtain a trained feature extraction network;
    S3-3: separately sending the validation sets corresponding to the eyeball position images and the lens position images into the trained feature extraction network separately corresponding the eyeball position images and the lens position images to obtain lens features corresponding to the eyeball position images and the lens position images;
    S3-4: evaluating states of the lens according to the lens features, comparing evaluation results with real labels in the validation sets, and recording a validation accuracy rate;
    S3-5: repeatedly performing steps S3-2 to step S3-4 according to a set number of times, saving weights of two feature extraction networks with a highest validation accuracy rate during a repeated performing process, taking the two feature extraction networks as a target feature extraction network group, and substituting the weights into the test sets to obtain a test accuracy rate of the target feature extraction network group; and
    S3-6: comparing the test accuracy rate with a target value, when the test accuracy rate is less than the target value, repeatedly performing step S3-5 until the test accuracy rate of the target feature extraction network group is greater than or equal to the target value, and using the target feature extraction network group corresponding to the test accuracy rate as the trained feature extraction network group.

6. The method according to claim 5, wherein the feature extraction network comprises an eyeball module corresponding to the eyeball position images and a lens module corresponding to the lens position images.

7. The method according to claim 6, wherein each of the eyeball module and the lens module comprises a back propagation neural network BPNN, wherein the back propagation neural network is trained by a convolutional neural network, a Fourier descriptor, and a gray-level co-occurrence matrix.

8. The method according to claim 7, wherein a specific step of training the feature extraction network comprises:
- S3-2-1: adjusting the eyeball position images and the lens position images to a required size, and performing a deformation processing to obtain deformed position images;
- S3-2-2: substituting the deformed position images into the Fourier descriptor to obtain 36-dimensional shape features corresponding to the deformed position images;
- S3-2-3: substituting the deformed position images into the gray-level co-occurrence matrix, and calculating energies, contrasts, entropies, and inverse differences of the gray-level co-occurrence matrix in four directions to obtain 16-dimensional texture features corresponding to the position images;
- S3-2-4: adopting an image dataset to pre-train the convolutional neural network to obtain a trained convolutional neural network, substituting the deformed position images into the trained convolutional neural network, and obtaining and using 2208-dimensional features of a penultimate layer of the trained convolutional neural network corresponding to the position images as depth features; and
- S3-2-5: fusing and then substituting the 36-dimensional shape features, the 16-dimensional texture features and the depth features into the back propagation neural network BPNN for training to obtain a trained back propagation neural network BPNN as the trained feature extraction network.

9. The method according to claim 8, wherein the deformation processing comprises random horizontal flip, random rotation of 0-10 degrees, brightness adjustment, color jitter, and normalization.

10. The method according to claim 7, wherein a step of obtaining the trained collaborative learning network comprises:
- S5-1: using a learning layer of the back propagation neural network BPNN in each of the eyeball module and the lens module as an input layer of a collaborative learning network;
- S5-2: adding two fully connected layers behind the input layer of the collaborative learning network, wherein, the two fully connected layers are used as a learning layer and an output layer of the collaborative learning network, and a result obtained from the output layer of the collaborative learning network is a prediction result; and
- S5-3: linking and substituting features correspondingly obtained by the eyeball module and the lens module into the input layer of the collaborative learning network to obtain the trained collaborative learning network.

* * * * *